(12) United States Patent
Aarts et al.

(10) Patent No.: US 8,979,731 B2
(45) Date of Patent: Mar. 17, 2015

(54) CALMING DEVICE

(75) Inventors: Ronaldus Maria Aarts, Geldrop (NL);
Joanne Henriette Desiree Monique Westerink, Eindhoven (NL); Johan Partomo Djajadiningrat, Eindhoven (NL); Johannes Willem Frens, Eindhoven (NL); Marius Cornelis Rozendaal, Amsterdam (NL)

(73) Assignee: Koninklijke Philips N.V., Eindhoven (NL)

( * ) Notice: Subject to any disclaimer, the term of this patent is extended or adjusted under 35 U.S.C. 154(b) by 608 days.

(21) Appl. No.: 13/057,489

(22) PCT Filed: Aug. 4, 2009

(86) PCT No.: PCT/IB2009/053377
§ 371 (c)(1),
(2), (4) Date: Feb. 4, 2011

(87) PCT Pub. No.: WO2010/015998
PCT Pub. Date: Feb. 11, 2010

(65) Prior Publication Data
US 2011/0137110 A1 Jun. 9, 2011

(30) Foreign Application Priority Data

Aug. 8, 2008 (EP) .................................. 08162047

(51) Int. Cl.
*A61M 21/02* (2006.01)
*A61M 21/00* (2006.01)

(52) U.S. Cl.
CPC ....... *A61M 21/02* (2013.01); *A61M 2021/0027* (2013.01); *A61M 2021/005* (2013.01);
(Continued)

(58) Field of Classification Search
CPC ............... A61B 5/0476; A61B 5/0205; A61B 5/04001; A61B 5/01; A61B 5/11; A61B 5/4519; A61B 5/0402; A61B 5/486; A61B 5/4809; A61B 5/04012; A61B 5/0482; A61B 5/4812; A61B 3/113; A61B 5/0006
USPC ................ 600/26–28, 544–546; 128/897–899
See application file for complete search history.

(56) References Cited

U.S. PATENT DOCUMENTS 3,855,998 A * 12/1974 Hidalgo-Briceno .......... 600/545
5,362,069 A * 11/1994 Hall-Tipping .................... 463/7
(Continued)

FOREIGN PATENT DOCUMENTS

GB         2234840 A    2/1991
KR     1020020042772 A    6/2002
(Continued)

OTHER PUBLICATIONS

"The Brightest Spot in an Otherwise Grey Existence"; Search Blog Regarding Insomnia Anad Falling Asleep Games, Retreived From http://brightgreyspot.blogspot.com/2007/04/falling-asleep-games.html., on Jun. 11, 2008, 4 Page Document.
(Continued)

*Primary Examiner* — Christine Matthews
*Assistant Examiner* — Joshua D Lannu

(57) ABSTRACT

A device (1), for calming down a subject, comprises a content delivering means (12,14) adapted for delivering a content in a first mode, at least one sensor (22, 24, 26, 28, 29) configured to detect an activity level of the subject and a controlling unit operatively coupled to the at least one sensor. The controlling unit receives the detected activity level and compares the detected activity level with a pre-determined threshold activity level. The controlling unit is capable of changing the delivery of the content to a second mode when the detected activity level is above the threshold activity level.

23 Claims, 2 Drawing Sheets

(52) U.S. Cl.
CPC .... *A61M2205/3375* (2013.01); *A61M 2230/04* (2013.01); *A61M 2230/06* (2013.01); *A61M 2230/205* (2013.01); *A61M 2230/42* (2013.01); *A61M 2230/63* (2013.01); *A63F 2300/1012* (2013.01); *A63F 2300/1081* (2013.01); *A63F 2300/1093* (2013.01); *A63F 2300/6027* (2013.01); *A63F 2300/6063* (2013.01); *A63F 2300/632* (2013.01); *A63F 2300/8094* (2013.01)
USPC ............................................. 600/27; 600/28

(56) References Cited

U.S. PATENT DOCUMENTS

| | | | | |
|---|---|---|---|---|
| 5,377,100 | A | * | 12/1994 | Pope et al. .................... 600/545 |
| 6,123,661 | A | * | 9/2000 | Fukushima et al. ............ 600/27 |
| 7,264,377 | B2 | | 9/2007 | Cooper et al. |
| 2006/0071784 | A1 | | 4/2006 | Frank |
| 2008/0006762 | A1 | * | 1/2008 | Fadell et al. ............... 250/201.1 |
| 2008/0073851 | A1 | | 3/2008 | Myers |

FOREIGN PATENT DOCUMENTS

| | | | |
|---|---|---|---|
| KR | 1020060103392 | A | 9/2006 |
| WO | 9935633 | A2 | 7/1999 |
| WO | 2004069319 | A1 | 8/2004 |
| WO | 2008009978 | A1 | 1/2008 |
| WO | WO 2008009978 | A1 * | 1/2008 |

OTHER PUBLICATIONS

Sleep Well 2.1+; Sleep Well Publisher's Description About an Audio Relaxation Technique, Retrieved From http://www.soft32.com/download_159512.html., on Jun. 11, 2008, 3 Page Document.

* cited by examiner

CALMING DEVICE

FIELD OF THE INVENTION

This invention relates to a calming device, in particular to a calming device that delivers content in a mode to calm down a subject.

BACKGROUND OF THE INVENTION

Sleeping well is an essential condition for good health and to a feeling of wellbeing in human beings. Unfortunately, many persons have problems falling asleep. Traditionally, mental exercises such as "counting sheep" are used as a means of lulling oneself to sleep. If the subject is a child, the best way to put him/her to sleep is to tell or read a story. Multimedia presentation is often considered to have a potential to impart the mental exercises or to deliver the stories, as it is complemented by both sound and visual effects. However, one of the problems with the existing multimedia devices is that they tend to excite the subject rather than calming them down. These devices adopt the high energy entertainment strategies of Hollywood movies and computer games in which the objective is to create 'an adrenaline rush'. These devices fail to lull one to sleep and also ignore the socio-cultural role of reading children a story which is usually to put them to sleep or at least to calm them down.

SUMMARY OF THE INVENTION

Therefore, it is the object of the invention to develop a device that ensures that a subject calms down and tends to fall asleep.

According to the invention, a device for calming down a subject comprises a content delivering means adapted for delivering a content in a first mode, at least one sensor configured to detect an activity level of the subject and a controlling unit operatively coupled to the at least one sensor, wherein the controlling unit is configured for receiving the detected activity level and for comparing the detected activity level with a pre-determined threshold activity level, and wherein the controlling unit is capable of changing the delivery of the content to a second mode when the detected activity level is above the threshold activity level. The delivery of the content is changed to the second mode based on the activity level of the subject. This mode change ensures that the subject remains calm and goes to sleep.

According to an embodiment of the invention, the controlling unit is capable of delivering the content in the first mode when the detected activity level is below or equals the threshold activity level. The controlling unit switches the delivering means back to the first mode when the activity level is lower than the pre-determined threshold value.

According to an embodiment of the invention, the content is a story, music or a game. If the subject to be put to sleep is a child, reading a story is one of the ways to put him/her to sleep. Games such as "counting sheep" are also used as a means of lulling oneself to sleep. Usually, this activity is depicted in cartoons, comic strips and other mass media as an endless series of identical white sheep jumping over a fence, while the number that do so is counted.

According to another embodiment of the invention, the activity level is detected by the at least one sensor by detecting a bodily movement and/ or a voice level of the subject, and/or by measuring heart rate and/or breathing rate of the subject, and/or by analyzing a sleeping stage of the subject. The activity level of the subject can be detected by detecting a physical or a physiological behavior. The bodily movement can be detected by a load sensor, a camera with an image analyzer, a motion sensor, a ferro-electret foil or a piezo foil. The bodily movement can be measured by a camera with image analysis, by load sensors placed under the bed of the subject which detect a change in weight distribution, by a movement sensor attached to the bed to detect shaking of the bed, a smart mattress or smart pillow which can analyze pressure points through piezo technology. The voice level can be detected by microphones. The voice level can be measured by relating a voice profile to amplitude so that the voice of the subject is distinguished from a voice narrating a story. These can be sound capture devices comprising microphones and filters which can distinguish between the child screaming or shouting and the voice of the narrator. The heart rate can be measured by classical electrical Ag/Ag Cl electrodes measuring the ECG signal, by ballistocardiogram, e.g. with a static charge sensitive bed (SCSB), or by a piezo foil, by an EMFi-film sensor build into a chair, by measuring the oxygen saturation ($SPO_2$), by measuring the (photo-)plethysmogram PPG, in the finger, ear or some other body part, by using non-galvanic capacitive electrodes, by using a wristwatch like device, by using seismosomnography, with the help of an ultra wide band radar, by using optical vibrocardiography, by acoustical with a microphone (phonocardiogram), by using an intelligent textile or an underwear with built in sensors. The breathing rate can be measured directly or indirectly. The direct methods measure a change of resistance in a resistor situated in the vicinity of nostrils and mouth of the subject, or with a band on the belly or breast of the subject. The change in resistance is caused by breathing. The indirect methods use a signal like ECG or PPG. The breathing rate is filtered out from these signals using filtering techniques. The sleeping stage can be analyzed by a hypnogram.

According to a preferred embodiment of the invention, the pre-determined threshold activity level can be varied for each subject. The threshold level is not a factory-defined setting but can be adjusted depending on the nature of the subject. If the subject is a child, each child needs different threshold levels, depending on their character and a parent can define the pre-determined threshold activity level. The pre-determined threshold activity level can also be adapted automatically over time to find the optimum timing to get the subject to sleep. This means that small variations in the threshold level are implemented over consecutive nights and those values belonging to the shortest route to sleep or calming down are retained.

According to an embodiment of the invention, the content delivering means comprises at least one sound generator for generating a sound in the first and second mode and at least one display means for displaying an image in the first and second mode. Such a content delivering means is considered as having the potential to tell children's stories in a compelling manner as the spoken word can be complemented by sound effects and movies.

According to yet another embodiment of the invention, wherein the content is a story, and wherein in the second mode, the sound generated has a reduced clarity and/or lower understandability as compared to the sound generated in the first mode. The delivery of the story is changed to the second mode when the activity level of the subject is higher than the threshold value. The activity level higher than the threshold level indicates that the subject is very energetic and not calm yet. Then the narration voice becomes softer resulting in reduced clarity and lower understandability. In other words, the subject is encouraged to calm down and lie still as otherwise he/she cannot listen to the story. Only when the subject is calm, he/she can fully enjoy the story as otherwise the sound becomes more difficult or less enjoyable to perceive. Changes in sound quality are obtained by decreasing the volume, by hushing the narration voice, by changing the acoustics, for example, by changing the echo or reverb, by fading out part of sound track (e.g. the narrative voice remains but the music sound track disappears).

According to an embodiment of the invention, wherein the content is a story, and wherein in the second mode the image has a reduced viewability and/or poorer aesthetic quality as compared to the image displayed in the first mode. The delivery of the story is changed to the second mode when the activity level of the subject is higher than the threshold value. The activity level higher than the threshold level indicates that the subject is very energetic and not calm yet. Then the image becomes blurred. In other words, the subject is encouraged to calm down and lie still as otherwise he/she cannot enjoy the story. Only when the subject is calm, he/she can fully enjoy the story as otherwise the image becomes less enjoyable to perceive. The image may become blurred either by changing the focus of a physical lens (i.e. a motor-driven lens steered away from auto-focus) or by applying digital blurring filters to the image/video in real-time or the image may become smaller (i.e. from wide-screen, via postcard sized, to a thumbnail). Other types of possible image processing are similar to image processing in PhotoShop or video processing in After Effects.

According to an embodiment of the invention, wherein the content is a story, and wherein the controlling unit is capable of switching the delivery of the content back to the first mode when the detected activity level is below or equals the threshold activity level.

When the detected activity level is lower than the threshold value, it indicates that the subject is calm and is concentrating on the story. When the subject is calm, the narration voice returns to normal and the images become fully visible again so that the subject is encouraged to keep calm.

According to yet another embodiment of the invention, the content is a story, and wherein the delivery of the content is changed from first mode to the second mode or from the second mode to first mode progressively. The switch over from first mode to second mode or vice versa happens gradually and thus ensures that the subject remains calm and relaxed.

According to another embodiment of the invention, wherein the content is a game, and wherein the game is played at a first level in the first mode and at a second level in the second mode. The games played at different levels ensure that the subject gets relaxed with each level and falls asleep.

According to a further embodiment of the invention, the second level is substantially easier as compared to the first level. The existing games have a typical characteristic that the degree of difficulty of playing the game is automatically increased as the game progresses. This results in a prolonged involvement of the subject. Inversion of the direction in which the degree of difficulty of the game can yield a very powerful means that can help people to fall asleep. As the games become increasingly easier to perform, the subject becomes increasingly bored or at least more relaxed and, in the end, falls asleep. This is based on the knowledge that simplicity, repetitiveness and rhythm all stimulate falling asleep.

According to a still further embodiment of the invention, wherein the content is a game, the controlling unit is further capable of delivering the game in different modes when the detected activity level is below or equals the threshold activity level. The low activity level indicates that the subject is relaxed. With the degree of relaxation of the subject, the degree of difficulty is adapted accordingly.

According to another embodiment of the invention, wherein the content is a game, the controlling unit is further capable of delivering the game in different modes as a function of time. Basic games according to the invention are self-adjusting, i.e. they become easier over time in an autonomous way.

According to yet another embodiment of the invention, the game is played at a different level in the different modes, and wherein each level is substantially easier as compared to the previous level. The idea behind this is to induce boredom while occupying the mind with something simple, repetitive and rhythmic, all of which are known to help humans to fall asleep.

According to another aspect of the invention, a method of calming down a subject comprises the steps of:
 a. switching on a content delivering means to deliver the content in a first mode;
 b. detecting activity level of the subject;
 c. comparing the detected activity level with a pre-determined threshold activity level; and
 d. changing the delivery of the content to a second mode when the detected activity level is above the threshold activity level.

DETAILED DESCRIPTION OF EMBODIMENTS OF THE INVENTION

Figure 1:
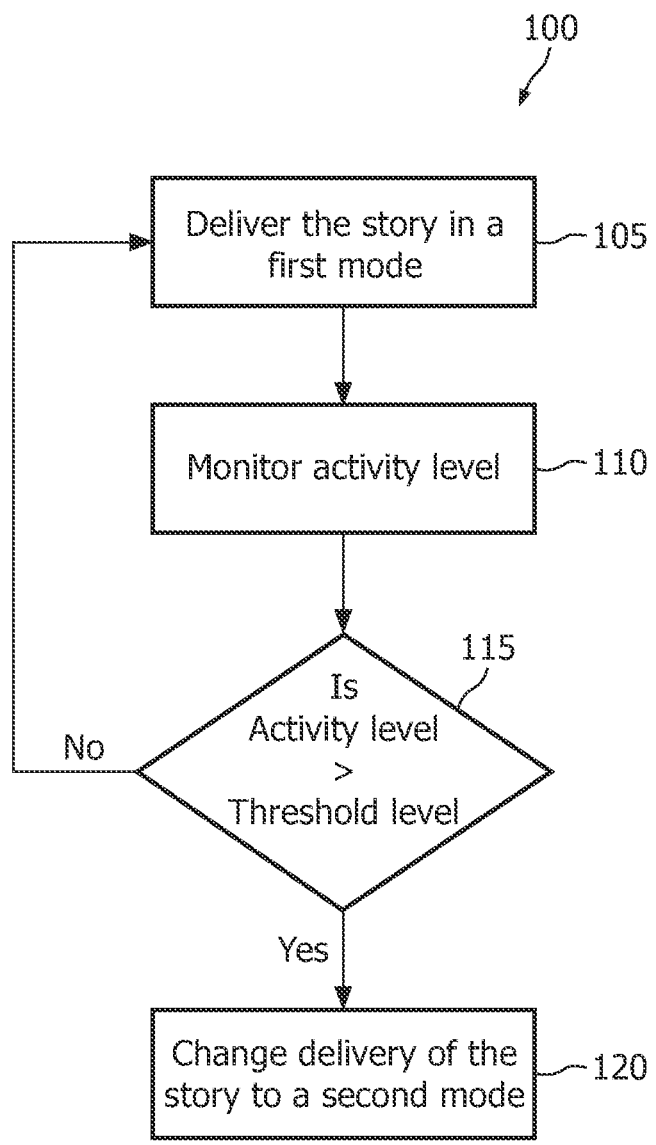
FIG. 1 is an exemplary flow chart of an embodiment of a method in accordance with some embodiments hereof.

The present invention will be described with respect to particular embodiments and with reference to certain drawings but the invention is not limited thereto. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The figures are merely schematic views of preferred embodiments according to the invention. In the figures, the same reference numbers refer to equal or corresponding parts.

Detecting an activity level, in the context of invention also means detecting calmness level of a subject. If the subject is more active, it means he is less calm and if the subject is less active, it means he is calmer, it means that when a subject is calm and sleepy, he is not physically active. The sensors measure physical activity and calmness can be derived from that. However, some sensors that measure heart beat and breathing rate may not directly measure physical activity, but they do give information about the sleepiness/calmness of a person.

FIG. 1 is an exemplary flow chart that illustrates a process 100 performed by a calming device 1 in accordance with an embodiment of the present invention. As indicated at 105, the calming device 1 delivers a story in a first mode. An activity level of a subject is monitored as shown at 110 at 115, a determination is made whether the monitored activity level is above a pre-determined threshold activity level. In the instance that the monitored activity level is above the pre-determined threshold activity level, the delivery of the story is changed to a second mode as shown at 120. In the instance that the monitored activity level is below the pre-determined threshold activity level, the delivery of the story continues in the first mode.

Figure 2:
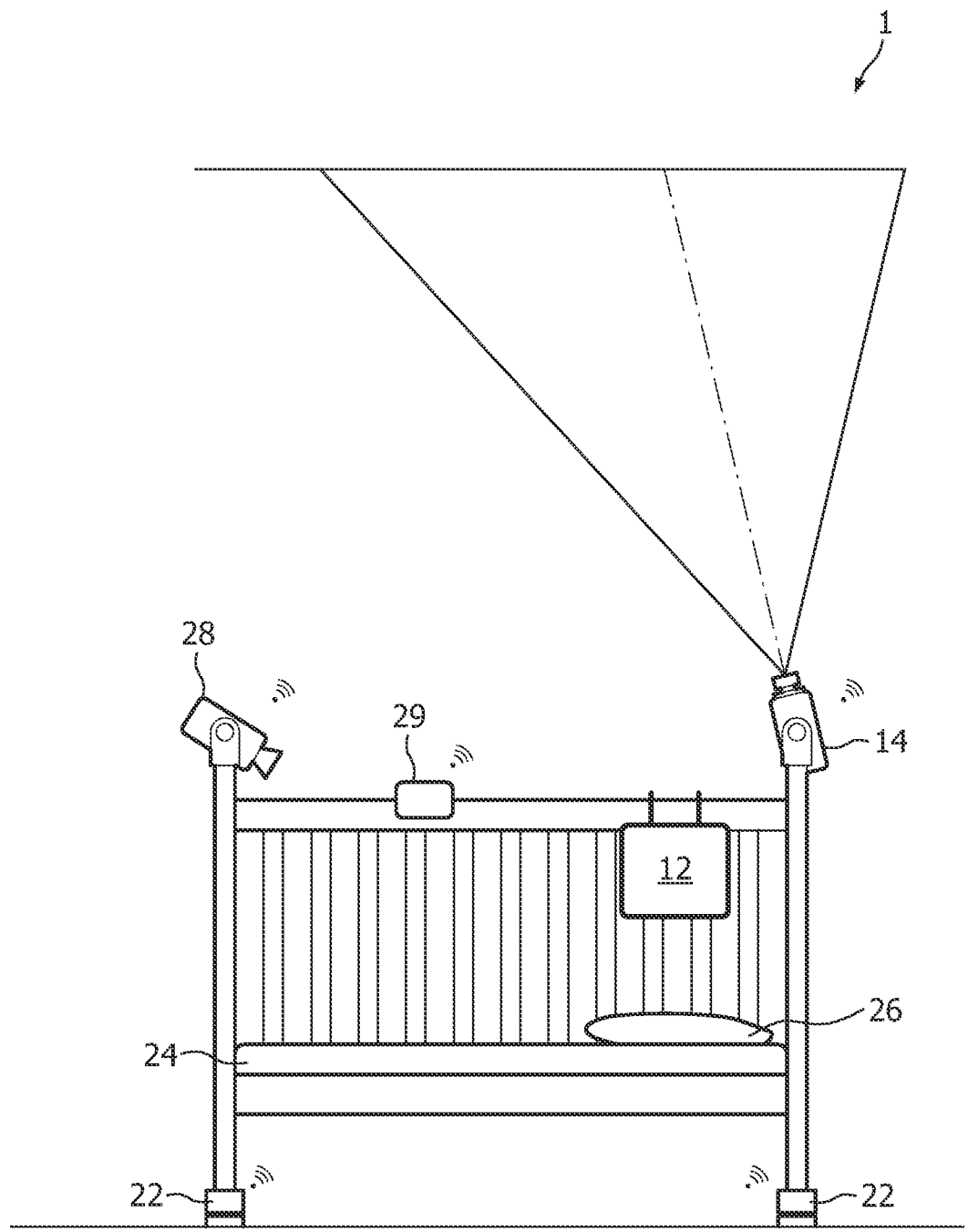
FIG. 2 is an exemplary illustration of an embodiment of a device according to some embodiments hereof.

Referring to FIG. 2, there is shown an exemplary illustration of an embodiment of a calming device 1, according to some embodiments hereof. The calming device includes a content delivering means 10 which may be a screen 12 or a wall/ceiling projector 14. It also may include a sound generating means (not shown). The calming device 1 comprises at least one sensor 20. The sensor may be a load sensor 22, a piezo mattress 24, a piezo pillow 26, a video camera 28 fitted with a motion detector or a motion sensor 29 to name a few. The calming device also includes a controlling unit 30 (not shown). The controlling unit with a microcontroller takes input from the sensor 20 and controls the content delivering means 10. The sensor 20, the content delivering means may be networked wirelessly to eliminate any entanglement danger for the subject. For example, the load sensor 22 under the bed is wirelessly connected to the controlling unit (which could be situated anywhere, may be attached to the wall, to the bed, placed on a bedside table or shelf) which in turn controls the content delivering means 10.

If the content is a story, the following steps are followed. The subject in this embodiment is preferably a child. A parent of the child chooses a threshold level to match the nature of the child. The parent then switches on the calming device 1 and chooses a story. The content delivering means 10 starts delivering the story. It could be delivered as an audio-book, as a visual or as an audio-visual story. The sensor 20 senses the child's activity level. If the activity level is below a pre-determined threshold activity level, the story is delivered to its full extent. If the activity level is above the threshold, the story deliverance becomes subdued. For example, narrative voice may start whispering, audio may become softer and the image may become blurred. The sound may become distorted so that the child can still acoustically hear the sound but not intelligibly understand it i.e. the child may not understand lyrics or may not recognize the melody any longer. The narration voice may become hushed. Parts of the sound track may disappear, for example, the narration voice, certain instruments (say the bass or melody instrument) or the whole music sound track may disappear. The image may become smaller or may be drained of its color. Above the activity threshold i.e., the more active the child is, the more subdued and the more difficult the story becomes to perceive and enjoy, thus encouraging the child to calm down. When the child's activity level drops, the story becomes more and more enjoyable to listen or to watch. When the child's activity level drops below the threshold, the story is again delivered to its fullest.

If the content is a game, they may become easier over time in an autonomous way. So, the most essential feature of this invention is the creation of electronic games that become increasingly easier to perform so that the subject becomes increasingly more bored or at least more relaxed and, in the end, falls asleep. Inversion of the direction in which the degree of difficulty of an electronic game develops over time, can yield a very powerful means that can help people to fall asleep. The simplicity, repetitiveness and rhythm of the game stimulate a subject to falling asleep. In a more preferred embodiment, the difficulty level of the game is changed based on a feedback received from the sensor 20. The sensor informs the controlling unit on the degree of relaxation of the subject and thus the degree of difficulty is changed accordingly. The games can comprise sound, images, or both the sound and the images. 3-D sound or localized sound may also be used. The nature of the game should be such that it should help the subject in getting increasingly more relaxed, i.e. sounds and images of the game should not cause arousal but rather boredom (e.g. no shooting sounds but rather soft, maybe yoga-like, sounds). In principle, any electronic game, that offers a diminishing degree of difficulty as the game progresses, can be used as a means for falling asleep.

The feedback information can be based e.g. on a measurement and analysis of the actual reaction time of the subject, as apparent from his or her reactions in the game. In a different embodiment, an analysis of the depth or the rhythm of the breathing of the subject can be used for feedback. Alternatively, the heart rate of the subject can be used as a feedback to the controlling unit. In a still more sophisticated scheme, analysis of the exact actual sleeping stage (e.g. from a hypnogram) of the subject is used for the feedback. In a different embodiment of the invention, the subject controls the game not via the usual joystick or such a similar device, but via his or her breathing pattern. Then, the controlling unit can influence the specific breathing pattern required in playing the game in such a way that falling asleep results or, at least, is facilitated.

It should be noted that the above-mentioned strategies are given as examples. The invention is not restricted to the embodiments described herein. It will be understood that many variants are possible.

Whilst specific embodiments of the invention have been described above, it will be appreciated that the invention may be practiced otherwise than as described. The description is not intended to limit the invention. Any reference signs in the claims shall not be construed as limiting the scope.

The invention claimed is:

1. A device for inducing relaxation in a subject, the device comprising:
   a. a content delivering means adapted for delivering a story said content delivering means comprising:
      at least one sound generator generating a sound in a first mode and in a second mode;
   b. at least one sensor configured to detect an activity level of the subject; and
   c. a controller operatively coupled to the at least one sensor, the controller being configured to execute:
      delivering the story in the first mode using the content delivering means, wherein in the first mode content is delivered with an initial setting value;
      receiving the detected activity level from the at least one sensor;
      comparing the detected activity level with a pre-determined threshold activity level;

determining said detected activity level is above said pre-determined threshold activity level; and changing the delivery of the story to the second mode when the detected activity level is above the threshold activity level wherein said delivered story in said second mode is altered from the initial setting value by at least one of: a reduced clarity and lower understandability as compared to the sound generated in the first mode and configured to reduce the subject's activity level.

2. The device of claim 1, wherein the activity level is detected by detecting at least one of: a bodily movement, a voice level, heart rate measurement, a breathing rate, and a sleeping stage.

3. The device of claim 1, wherein the threshold activity level is varied for each subject.

4. The device of claim 1, further comprising:
at least one display means displaying an image in the first mode and the second mode.

5. The device of claim 4, wherein in the second mode the image displayed has a reduced viewability as compared to the image displayed in the first mode, wherein the reduced viewability is one of: blurred, smaller, and drained of color.

6. The device of claim 1, the controller further configured to:
switch the delivery of the story to the first mode when the detected activity level is below or equals thee threshold activity level.

7. The device of claim 1, wherein the controller is further configured to:
change the delivery of the story from the first mode to the second mode or from the second mode to the first mode progressively.

8. A method of inducing relaxation in a subject, executed in a computer system, said method causing the computer system to execute the steps comprising:
delivering content in a first mode with an initial setting value;
detecting an activity level of the subject;
comparing the detected activity level with a pre-determined threshold activity level;
determining said detected activity level is above said pre-determined threshold activity level; and
changing the delivery of the content to a second mode when the detected activity level is above the threshold activity level by altering at least one of: a loudness, and an image, wherein said delivered content in said second mode is altered from the initial setting value and configured to reduce the subject's activity level, said alteration including at least one of a reduced audio clarity and a reduced visual clarity.

9. The method according to claim 8, wherein the content is one of: a story, a music, and a game.

10. The method according to claim 9, the method further comprising:
switching the delivery of the content to the first mode when the detected activity level is below or equals the threshold activity level.

11. The method according to claim 8, wherein the content is a game, the method further comprising:
switching the delivery of the content to different modes when the detected activity level is below or equals the threshold activity level, wherein the game is played at different levels in each mode, and wherein a level of the second mode is more repetitive or rhythmic than a level of the first mode.

12. A device for inducing relaxation in a subject, thee device comprising:
a. a content delivering means adapted for delivering a story in different modes, said content delivering means comprising:
at least one display means displaying an image in a first mode and in a second mode;
b. at least one sensor configured to detect an activity level of the subject; and
c. a controller operatively coupled to the at least one sensor, the controller being configured to execute:
delivering the story in the first mode using tile content delivering means, wherein in the first mode content is delivered with an initial setting value;
receiving the detected activity level from the at least one sensor; comparing the detected activity level with a pre-determined threshold activity level;
determining said detected activity level is above said pre-determined threshold activity level; and
changing the delivery of the story to the second mode when the detected activity level is above the threshold activity level, wherein said delivered story in said second mode is altered from the initial setting value by at least one of: blurred, smaller, and drained of color and configured to reduce the subject's activity level.

13. The device of claim 12, wherein the activity level is detected by detecting at least one of: a bodily movement, a voice level, heart rate measurement, a breathing rate, and a sleeping stage.

14. The device of claim 12, wherein the threshold activity level is varied for each subject.

15. The device of claim 12, further comprising:
at least one sound generator generating a sound in the first mode and in the second mode, wherein in the second mode the sound generated by said at least one sound generator is altered and has at least one of: a reduced clarity and lower understandability as compared to the sound generated by said at least one sound generator in the first mode.

16. The device of claim 12, wherein the controller is further configured to execute:
switching the delivery of the story to the first mode when the detected activity level is below or equals the threshold activity level.

17. The device of claim 12, wherein the controller is further configured to execute:
changing the delivery of the story from the first mode to the second mode or from the second mode to the first mode progressively.

18. A device for inducing relaxation in a subject, the device comprising:
a. a content delivering means adapted for delivering a game, wherein the game is delivered at a first level in a first mode and at a second level in a second mode;
b. at least one sensor configured to detect an activity level of the subject; and
c. a controller operatively coupled to the at least one sensor, the controller being configured to execute:
delivering said game in the first mode using the content delivering means, wherein in the first mode of said game is delivered with an initial setting value;
receiving the detected activity level from the at least one sensor;
comparing the detected activity level with a pre-determined threshold activity level;

determining said detected activity level is above said pre-determined threshold activity level; and changing the delivery of the game to the second mode when the detected activity level is above the threshold activity level wherein operation of the game in the second level is more repetitive or rhythmic than operation of the game in the first level.

19. The device of claim 18, wherein the controller is further configured to execute:

delivering the game in different modes when the detected activity level is below or equals the threshold activity level.

20. The device of claim 18, wherein the controller is further configured to execute:

delivering the game in different modes when the detected activity level is below or equals the threshold activity level.

21. The device of claim 18, wherein performing a task in said second level is different than performing said task in said first level.

22. The device of claim 18, wherein the controller is further configured to execute:

switching the delivery of the game to the first level when the detected activity level is below or equals the threshold activity level.

23. The device of claim 18, wherein the controller is further configured to execute:

changing the delivery of the game progressively from the first level to the second level or from the second level to the first level.

* * * * *